US011850179B2

(12) United States Patent
Kreutel et al.

(10) Patent No.: US 11,850,179 B2
(45) Date of Patent: *Dec. 26, 2023

(54) ORTHOPEDIC DEVICE

(71) Applicant: Ottobock SE & Co. KGaA, Duderstadt (DE)

(72) Inventors: Meike Kreutel, Cologne (DE); Charlotte Marquardt, Buxtehude (DE); Torsten Parth, Egelsbach (DE); Markus Tüttemann, Waltrop (DE); Carsten Vogel, Duderstadt (DE); Jonas Bornmann, Duderstadt (DE); Benjamin Schirrmeister, Göttingen (DE); Paula Klinkert, Frankfurt am Main (DE); Oliver Mizera, Kassel (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/534,247

(22) Filed: Nov. 23, 2021

(65) Prior Publication Data

US 2022/0079796 A1 Mar. 17, 2022

Related U.S. Application Data

(63) Continuation of application No. 16/947,088, filed on Jul. 17, 2020, now Pat. No. 11,259,949.

(51) Int. Cl.
*A61H 1/02* (2006.01)
*A61F 5/02* (2006.01)
(Continued)

(52) U.S. Cl.
CPC ............ *A61F 5/028* (2013.01); *A61F 5/0104* (2013.01); *A61H 1/0292* (2013.01);
(Continued)

(58) Field of Classification Search
CPC .... A61F 5/028; A61F 2005/0197; A61F 5/01; A61F 2005/0179; A61F 2005/0132;
(Continued)

(56) References Cited

U.S. PATENT DOCUMENTS

| 443,113 | A | | 12/1890 | Ray |
| 5,054,476 | A | * | 10/1991 | Petrofsky .............. A61F 5/0125 482/66 |

(Continued)

FOREIGN PATENT DOCUMENTS

| AU | 2018256552 A1 | 5/2019 |
| CH | 663897 A5 | 1/1988 |

(Continued)

OTHER PUBLICATIONS

English translation for CN 110666783, machine translated by SEARCH clarivate analytics, translated on Jan. 12, 2023.*

(Continued)

*Primary Examiner* — Tu A Vo
(74) *Attorney, Agent, or Firm* — HOLLAND & HART LLP

(57) ABSTRACT

An orthopedic device for supporting a lower back of a user includes
a mechanical energy store,
a pelvic element,
an upper body element with a first force transmission element and
an upper leg element with a second force transmission element.
The upper leg element is arranged on the pelvic element such that it can be swivelled about a first swivel axis,
the upper body element is movably arranged relative to the pelvic element, (Continued)

the first force transmission element can be engaged and disengaged with the second force transmission element by moving the upper body element relative to the pelvic element, and the mechanical energy store can be charged and discharged by swivelling the upper leg element relative to the upper body element when the first force transmission element is engaged with the second force transmission element.

19 Claims, 10 Drawing Sheets

(51) Int. Cl.
  *B25J 9/00* (2006.01)
  *A61F 5/01* (2006.01)
(52) U.S. Cl.
  CPC .............. *B25J 9/0006* (2013.01); *A61F 5/024* (2013.01); *A61F 2005/016* (2013.01); *A61F 2005/0155* (2013.01); *A61F 2005/0162* (2013.01); *A61F 2005/0179* (2013.01); *A61F 2005/0197* (2013.01); *A61H 2201/1238* (2013.01); *A61H 2201/163* (2013.01); *A61H 2201/1642* (2013.01); *A61H 2201/1673* (2013.01); *A61H 2205/081* (2013.01)
(58) Field of Classification Search
  CPC .. A61F 5/0102; A61F 2005/016; A61F 5/024; A61F 5/0104; A61F 2005/0155; A61F 2005/0162; A61H 1/0292; A61H 2201/1238; A61H 2201/163; A61H 2201/1642; A61H 2201/1673; A61H 2205/081; A61H 1/0244; A61H 1/0262; A61H 3/00; A61H 2201/1652; A61H 2201/1628; A61H 2003/007; A61H 2201/1215; B25J 9/0006; A63B 21/00178; A63B 21/0004; A63B 23/04
  See application file for complete search history.

(56) References Cited

U.S. PATENT DOCUMENTS

| | | |
|---|---|---|
| 6,436,065 B1 | 8/2002 | Mitchell |
| 10,524,974 B2 * | 1/2020 | Tung ............... A61H 1/0244 |
| 11,259,949 B2 * | 3/2022 | Kreutel ............ A61H 1/0292 |
| 11,638,673 B2 * | 5/2023 | Chen ................... A61H 1/00 601/5 |
| 2008/0161738 A1 * | 7/2008 | Giesen ............... A61F 5/026 602/19 |
| 2008/0287847 A1 | 11/2008 | Pansiera |
| 2011/0098617 A1 * | 4/2011 | Ferguson ............ A61F 5/026 602/16 |
| 2012/0271207 A1 | 10/2012 | Schoen |
| 2013/0131560 A1 * | 5/2013 | Ferguson ............ A61F 5/026 601/33 |
| 2013/0253393 A1 | 9/2013 | Schilling |
| 2014/0024978 A1 * | 1/2014 | Killian .................. A61H 3/00 601/33 |
| 2015/0230964 A1 | 8/2015 | Kazerooni et al. |
| 2016/0038313 A1 | 2/2016 | Kim |
| 2016/0250062 A1 | 9/2016 | Radaelli et al. |
| 2017/0014993 A1 | 1/2017 | Barnes |
| 2017/0196712 A1 | 7/2017 | Kazerooni et al. |
| 2017/0246740 A1 | 8/2017 | Barnes |
| 2017/0360588 A1 | 12/2017 | Yangyuenthanasan et al. |
| 2018/0161188 A1 | 6/2018 | Zistatsis |
| 2019/0015286 A1 | 1/2019 | Glaister et al. |

FOREIGN PATENT DOCUMENTS

| | | | | |
|---|---|---|---|---|
| CH | 106659629 A | | 5/2017 | |
| CN | 104822346 A | | 8/2015 | |
| CN | 105078703 A | | 11/2015 | |
| CN | 108471865 A | | 8/2018 | |
| CN | 110623817 A | * | 12/2019 | |
| CN | 110666783 A | * | 1/2020 | ............. B25J 17/00 |
| EP | 2645968 B1 | | 11/2011 | |
| WO | 2014195373 A1 | | 12/2014 | |
| WO | 2018178897 A1 | | 10/2018 | |

OTHER PUBLICATIONS

English translation for CN 110623817, machine translated by SEARCH clarivate analytics, translated on Jan. 12, 2023.*
International Search Report issued in International Application No. PCT/EP2020/069984, dated Oct. 28, 2020, 3 pgs.
Search Report dated Jul. 1, 2023; Chinese Patent Application No. 202080051785.9; 12 pages.

* cited by examiner

ORTHOPEDIC DEVICE

CROSS-REFERENCE TO RELATED APPLICATIONS

This is a continuation application from U.S. patent application Ser. No. 16/947,088, filed 17 Jul. 2020, which claims the benefit of German Patent Application No. 102019119645.0, filed 19 Jul. 2019, the disclosures of which are hereby incorporated, in their entireties, by this reference.

TECHNICAL FIELD

The invention relates to an orthopedic device for supporting a lower back of a user.

Such devices have been known from the prior art for many years and are used especially for lifting in order to provide support to the person who is to lift, for instance, a heavy object. Moreover, such devices are used for persons who have to work in a bent position.

BACKGROUND

This type of device is described, for instance, in U.S. Pat. No. 443,113 A1. It features upper leg elements that are arranged on the upper leg of the wearer. The device is also arranged on the upper body of the wearer via shoulder straps. Leaf spring elements are situated between the shoulder straps and the upper leg elements, said leaf spring elements being bent when bending down and thereby charged with potential energy. This causes the leaf spring elements to exert a force on the upper body that supports the extension of the body. However, it is disadvantageous that the resulting force is always exerted when an angle between the upper body and the upper leg changes. For example, it is exerted when climbing stairs or sitting, which is at the very least uncomfortable, but possibly even disruptive and uncomfortable.

Devices that work on a similar principle are known, for example, from US 2017/0196712 A1 and US 2017/0360588 A1. However, the force that supports the lower back or the upper body, which should make it easier for the person to straighten up, is not always exerted. In the formerly named prior art, the force is only exerted when a certain angle of inclination, i.e. when the angle between the upper body element of the device and the upper leg element of the device is smaller than a pre-determined angle, is exceeded. Up until this angle, the upper body can be inclined relative to the upper leg without charging an actuator or energy store. Nevertheless, in the case of this device, a supporting force always acts when the upper body assumes an angle relative to the upper leg that is smaller than a pre-determined threshold angle, i.e. the upper body is inclined relative to the upper leg.

The latterly named prior art comprises a device with which the supporting force is always exerted when the upper body assumes a pre-determined angle relative to the vertical, i.e. in the direction along which the weight force acts. This prevents the force from acting, for instance, when the wearer of the device sits, provided that the upper body does not exceed the pre-determined angle to the vertical. However, if the person leans so far when sitting that the pre-determined angle is exceeded, a supporting force is automatically exceeded.

The prior art includes various possibilities for moving a joint from an active state, in which, for example, a movement is freely possible, into a passive or braked position, in which, for instance, the movement is no longer possible or is only possible against a resistance. For example, EP 2 645 958 B1 describes a joint where this switch occurs magnetically.

The disadvantage of all the above-named options is that secure adjustment is not possible and it cannot be ensured that the force is only exerted when it is needed and wanted; rather, situations and movements may also occur that do not require a supporting force or the lower back need not be strained or supported. The invention thus aims to propose an orthopedic device which eliminates or at least mitigates these disadvantages of the prior art.

SUMMARY

The invention solves the problem by way of an orthopedic device for supporting a lower back of a wearer, wherein the device comprises a mechanical energy store, a pelvic element, an upper body element with a first force transmission element, and an upper leg element with a second force transmission element. Here, the upper leg element is arranged on the pelvic element such that it can be swivelled about a first swivel axis. The upper body element can also be moved relative to the pelvic element. The first force transmission element can be engaged and disengaged with the second force transmission element by moving the upper body element relative to the pelvic element. The mechanical energy store can be charged and discharged by swivelling the upper leg element relative to the upper body element when the first force transmission element engages with the second force transmission element.

The Invention is based on the knowledge that the lower back does not always need supporting when an angle between an upper body element, which is arranged, for instance, in the chest or back area of the upper body of wearer, and the lower leg element of the wearer is smaller than a pre-determined angle, i.e. when the two body parts are swivelled in relation to one another. Rather, support is only necessary when a swivelling occurs between the upper body, I.e. the chest of the wearer, and the pelvis of the wearer. The device according to the invention ensures that a supporting force is always exerted when this swivelling between the upper body and the pelvis of the wearer occurs. Conversely, if the upper body swivels relative to the upper leg such that it does not cause a movement of the upper body relative to the pelvis, a force should not be exerted.

The first force transmission element and the second force transmission element are designed in such a way that a force can be transmitted between them when they are engaged with one another, and a force cannot be transmitted when they are disengaged. Moreover, they are designed such that they can be engaged and disengaged multiple times. Preferably, these two elements are positive-locking elements and/or force-locking elements; it is especially preferable if they are two frictional-locking elements.

According to the invention, the upper body element, which is preferably arranged on the back or chest of the wearer, has to be moved relative to the pelvic element, which is preferably arranged on the pelvis of the wearer, in order to engage the first force transmission element with the second force transmission element. Only then can the energy store be charged or discharged with mechanical energy by way of further swivelling. Without this movement of the upper body element relative to the pelvic element, the two force transmission elements remain disengaged and a movement of the upper leg element relative to the upper body element does not result in the charging of the energy store. It is thus also not possible for a force that supports the extension to be applied.

Preferably, the mechanical energy store comprises at least one spring element or is a spring element. Alternatively or additionally, it features at least one pressure accumulator, a pneumatic and/or hydraulic system and/or a hydraulic energy store.

The configuration according to the invention of the orthopedic device ensures that no additional force that supports the extension is applied during sitting or climbing stairs, which generally involves insufficient movement between the upper body element and the pelvic element, whereas the lifting of a heavy object, for example, is supported. In the case of such movements, the upper body element moves relative to the pelvic element, thereby engaging the first force transmission element with the second force transmission element. In this state, if the upper leg element is swivelled relative to the pelvic element, the mechanical energy store is charged with potential energy, which causes a force that supports the extension to be applied.

In a preferred configuration, the first force transmission element comprises a gearwheel that is eccentrically arranged on the pelvic element such that it can be swivelled. In this configuration, the second force transmission element is preferably a gearwheel that is arranged on the upper leg element such that it is torque-proof.

The upper body element is preferably connected to the first force transmission element and in particular to the gearwheel of the first transmission element in such a way that the first force transmission element is swivelled about the second swivel axis when the upper body element is moved relative to the pelvic element. This movement causes the gearwheel of the first force transmission element to come into contact and engage with the second force transmission element, which preferably also features a gearwheel. In this state, if the upper leg is moved relative to the upper body, for example if the wearer kneels down, the mechanical energy store is charged with potential energy.

In the case of the reverse movement, this potential energy is initially released by the exertion of a force on the upper leg and/or the upper body of the wearer that supports the extension of the body of the wearer. It is not until the upper body—and thus the upper body element attached to it—is moved relative to the pelvis—and thus to the pelvic element attached to the pelvis—that the first force transmission element disengages with the second force transmission element and the mechanical energy store cannot be re-charged or further discharged.

The upper body element and the first force transmission element preferably have connection elements that correspond with one another, so that the upper body element can be connected to the first force transmission element in multiple positions. In this way, for instance, the upper body element may feature a projection or peg or pin that can be introduced into recesses or indentations on the first force transmission element. The reverse configuration is of course also possible, in which the first force transmission element has a projection, peg or pin and the recesses and indentations are situated on the upper body element. Regardless of the actual configuration, it is advantageous if the upper body element and the first force transmission element can be fixed in different positions and orientations relative to one another. It is especially preferable if these different positions mean that the first force transmission element is positioned at different angular positions about the second swivel axis. This renders it possible to adjust the strength with which the upper body element must be moved relative to the pelvic element to engage the two force transmission elements. It is therefore possible to set the point during a movement at which the mechanical energy store can be charged.

It is particularly preferable if the orthopedic device has a displacement device that is configured to move the first transmission element and/or the second force transmission element towards one another when the upper body element assumes an angle in relation to the pelvic element that is smaller than a pre-determined threshold angle. The angle between the upper body element and the pelvic element is approximately 180° when the wearer of the device is standing upright. If he bends over or tilts his upper body relative to the pelvic element, this angle becomes smaller. Should the angle pass the pre-determined threshold value, the angle is then smaller than this pre-determined threshold angle, so that the displacement device moves the two force transmission elements towards each other. The displacement device preferably moves either the first force transmission element or the second force transmission element, while the respective other force transmission element remains in place. Alternatively, the displacement device moves both the first and the second force transmission element.

In contrast to the configuration described above, in which the two force transmission devices are continuously moved towards one another upon a movement of the upper body element relative to the pelvic element and engage with one another upon reaching the threshold angle, with the configuration described here, there is no initial movement of the two force transmission elements towards one another. Only when the angle between the upper body element and the pelvic element passes the pre-determined threshold angle does the movement described here occur, so that the two force transmission elements are subsequently engaged.

It is particularly preferable if the displacement device is configured to move the first transmission element and/or the second force transmission element away from one another when the upper body element assumes an angle in relation to the pelvic element that is greater than the pre-determined threshold angle.

To move the first force transmission element and/or the second force transmission element, the displacement device is configured to exert a force on the force transmission element that is to be moved. It has been proven beneficial for this force to be maintained once the respective force transmission element has been moved and the two force transmission elements engaged or disengaged. This ensures that no inadvertent change in state occurs. If the two force transmission elements are engaged via a force of the displacement device, the force used to achieve this is maintained so as to prevent the two force transmission elements from inadvertently disengaging, which would adversely affect the functionality of the orthopedic device. The same applies for the force that disengages the two force transmission elements. This force is also preferably maintained so as to prevent an inadvertent displacement of the respective force transmission element, which would cause the two force transmission elements to re-engage.

Preferably, at least two magnets are arranged on the pelvic element or the upper leg element and at least one magnet is arranged on the respective other element in such a way that they exert a force on one another, the direction of which changes when, during a movement of the upper body element relative to the pelvic element, the angle passes the pre-determined threshold angle. In this configuration, the displacement device thus features the magnets specified. On the element on the upper body element or the pelvic element on which two magnets are arranged, said magnets are preferably arranged in a different orientation. This means that for at least one of the magnets, the north pole is directed towards the respective other element of the orthopedic device, and for at least one other magnet, the south pole is directed towards the respective other element.

If the angle between the upper body element and the pelvic element is greater than the pre-determined threshold angle, the two force transmission elements are not engaged with one another. This preferably causes the application of a force that keeps the two force transmission elements apart. This may be achieved by the magnets exerting a force on one another. For example, this may be a repelling force. This is achieved by positioning one magnet of the pelvic element and one magnet of the upper leg element close to each other, so that the same poles, i.e. the south pole or the north pole, are directed towards one another. If the pelvic element is now moved relative to the upper leg element, the magnets arranged on the respective elements are also moved. This results in a displacement of the moving magnets towards each other. At the point at which the angle of the upper body element relative to the pelvic element passes the pre-determined threshold angle, a second magnet of the pelvic element or the upper leg element preferably moves into the region of the at least one magnet of the respective other element. This results in an attractive force, as opposite poles of the two magnets are directed towards one another.

The orthopedic device can preferably be brought into an active and a passive state. The active state has already been described and is characterized by the fact that the first force transmission element and the second force transmission element can be engaged and disengaged by moving the upper body element relative to the pelvic element. This is not possible in the passive state. When in the passive state, if the upper body element is moved relative to the pelvic element, the two force transmission elements do not engage or disengage.

The device preferably features at least one activation element, the activation of which allows for the device to be brought from the active state into the passive state, and/or vice-versa. Such an activation element renders it possible to, for instance, decouple a movement of the first force transmission element from the movement of the upper body element. A reactivation of the activation element re-couples the movement, so that the force transmission elements can be engaged.

The mechanical energy store preferably has at least one spring element, preferably a spiral spring.

BRIEF DESCRIPTION OF THE DRAWINGS

In the following, some examples of embodiments of the present invention will be explained in more detail by way of the attached figures: They show.

DETAILED DESCRIPTION

Figure 1:
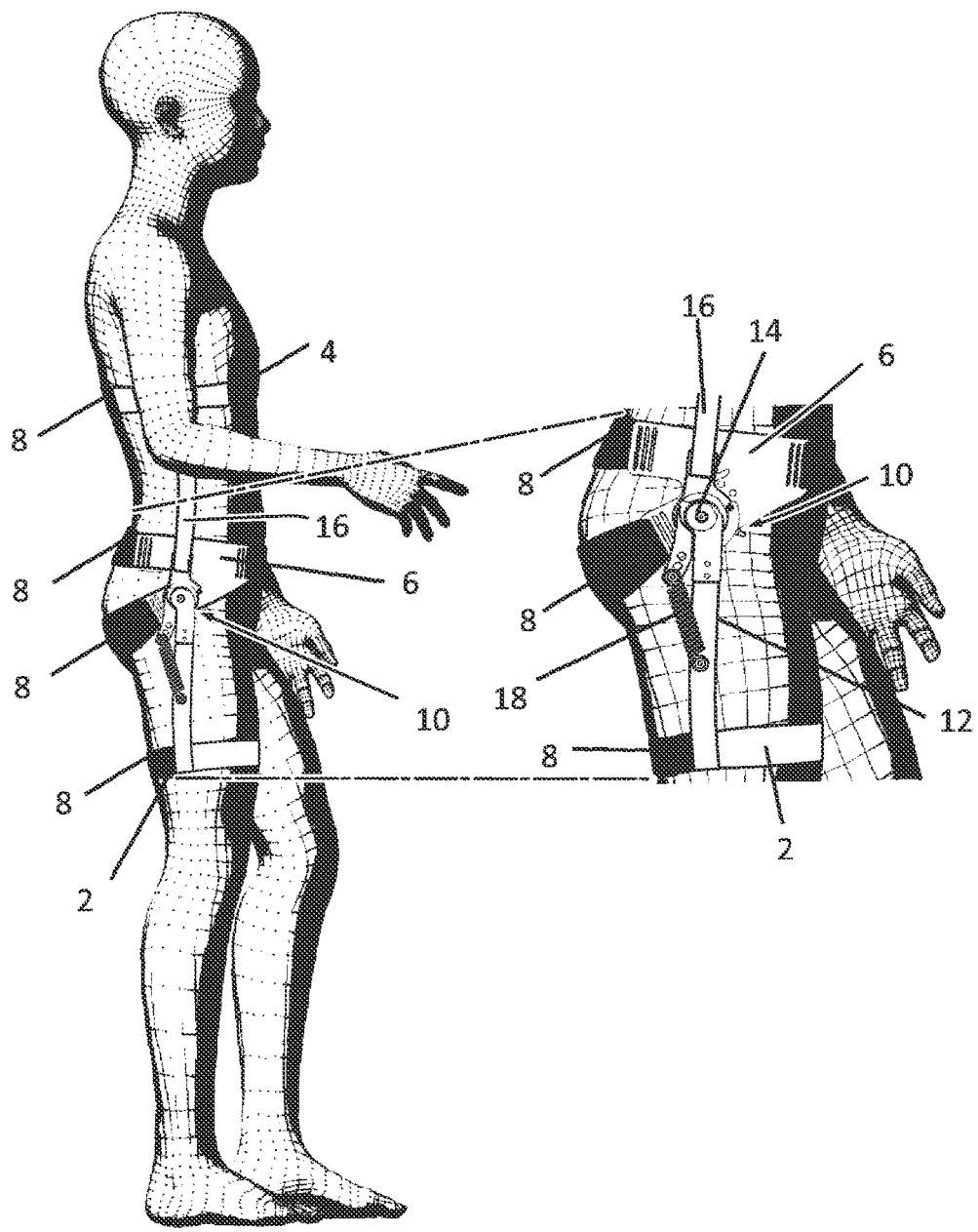
FIG. 1—an orthopedic device according to a first example of an embodiment of the present invention in the applied state, FIGS. 2 and 3—a section of the device in various views, FIG. 4—an exploded representation of the section from FIGS. 2 and 3, FIG. 5—the representation of the section in a partially dismantled state, FIGS. 6 to 8—representations of a section of a further embodiment of the present invention, FIGS. 9 to 10—schematic representations of a section of a further embodiment of the present invention, FIGS. 11 to 12—schematic representations of a section of a further embodiment of the present invention and FIGS. 13 to 15—representations of an embodiment of the invention in the applied state.

FIG. 1 shows the orthopedic device in an applied state. It comprises an upper leg element 2, which is arranged on an upper leg of the user, and an upper body element 4, which is arranged on the upper body. The device also features a pelvic element 6, which is arranged on the pelvis of the user. Both the pelvic element 6 and the upper leg element 2 as well as the upper body element 4 are arranged on the respective body part of the user.

The orthopedic device also has a joint device 10, which performs several functions in the example of an embodiment shown. On the one hand, the upper leg element 2 is arranged about a first swivel axis 14 on the pelvic element 6 via a first splint 12. The upper body element 4 is also arranged on the pelvic element 6 via a second splint 16 such that it can be swivelled, wherein the swivel axis coincides with the first swivel axis 14 in this example of an embodiment.

The orthopedic device also has a mechanical energy store 18, which is a tension spring in the example of an embodiment shown.

Figure 2:
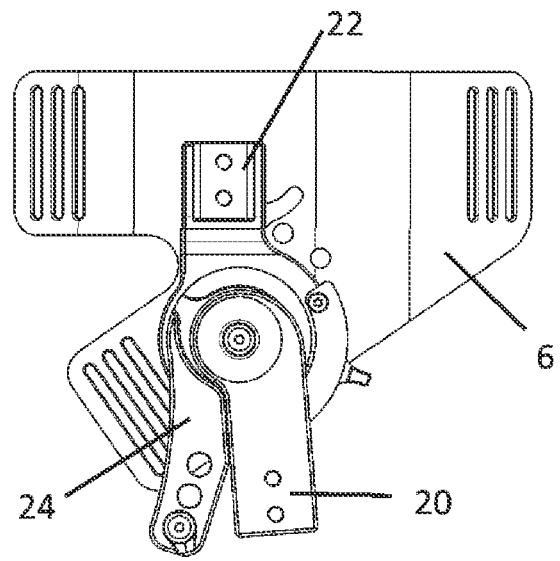

FIG. 2 depicts an enlarged representation of the pelvic element 6. One recognizes a first connection element 20, on which the first splint 12 of the upper leg element 2 is to be arranged, and a second connection element 22, on which the second splint 16 of the upper body element 4 is arranged. A lever 24 is provided, on which the mechanical energy store 18 is positioned.

Figure 3:
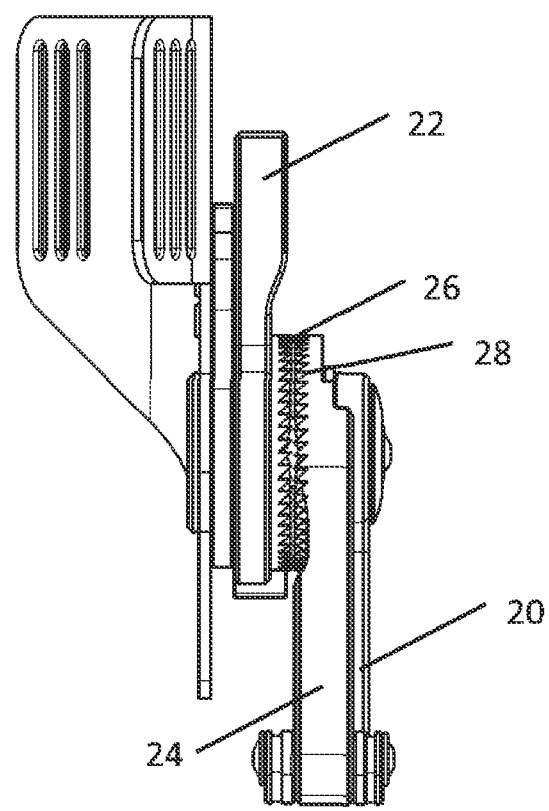
Figure 4:
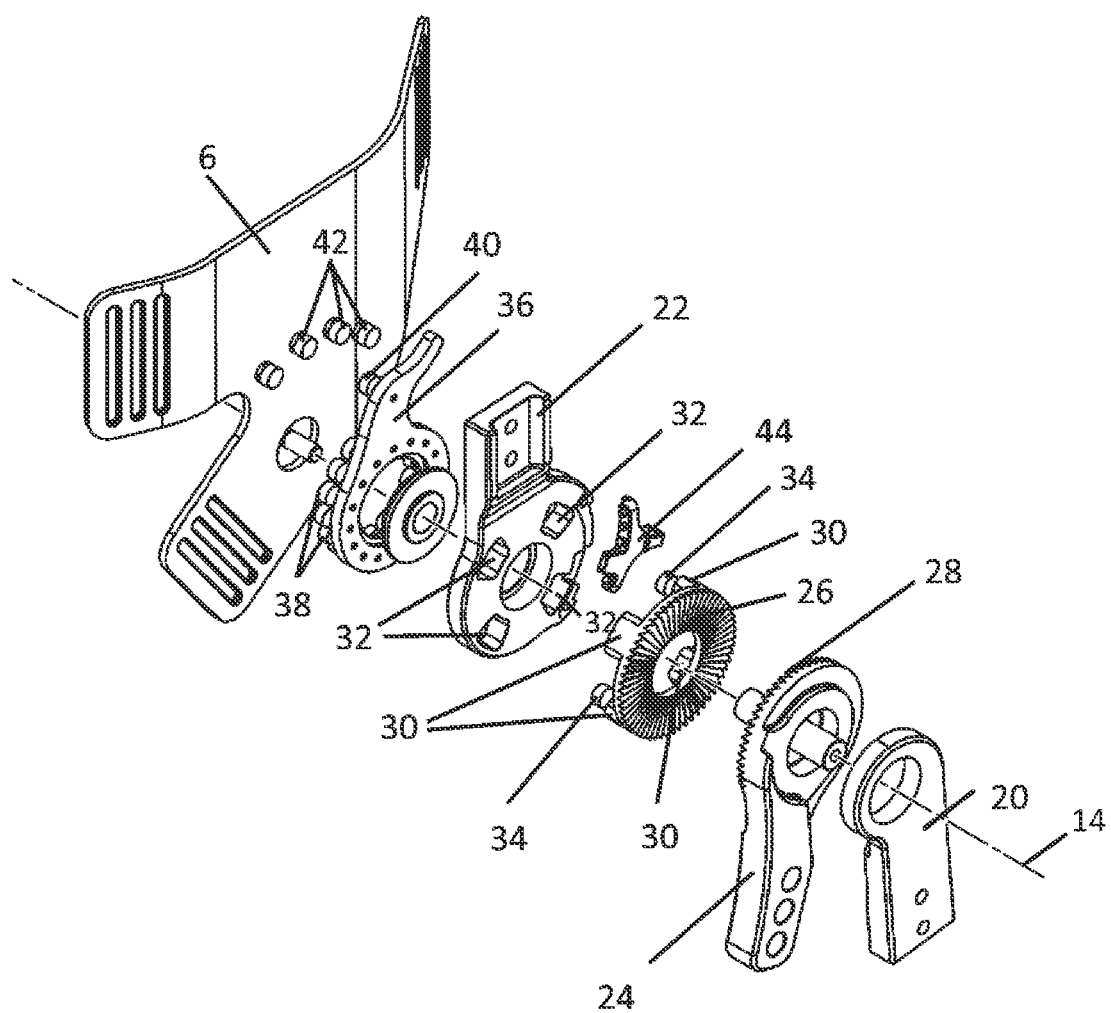

FIG. 3 depicts a side view of the device from FIG. 2. A first force transmission element 26, which is designed as a front gearwheel in the example of an embodiment shown, is situated on the second connection 22, which forms part of the upper body element 4. A corresponding second force transmission element 28 is positioned on the lever 24, which forms part of the upper leg element 2. The exploded view in FIG. 4 shows how it functions. The second force transmission element 28 is situated on the lever 24. The first force transmission element 26 is found as a separate component on the second connection element 22. It features four projections 30, which engage in four specially provided openings 32 on the second connection element 22. In FIG. 4, it can be recognized that a magnet 34 is arranged on two of the projections 30, wherein said magnet protrudes through the respective openings 32 when in the applied state. A displacement device 36 is arranged on the actual cover element such that it is torque-proof, said displacement device also comprising a series of magnets 38. In the example of an embodiment shown, they extend across the entire circumference of the displacement device 36, thereby affecting the magnets 34 on the first force transmission element 26. At the upper end of the displacement device 36 shown in FIG. 4, a positioning magnet 40 is depicted, which interacts with corresponding counter-magnets 42 that are arranged on the pelvic element 6. The positioning magnet 40 and the counter-magnets 42 are arranged such that opposite poles are directed towards one another. In the example of an embodiment shown, the displacement device 36 can thus be fixed on four different positions relative to the pelvic element 6 such that it Is torque-proof.

If the upper body element 4 and therefore the second connection element 22 is now twisted relative to the pelvic element 6, the position of the magnets 34 relative to the magnets 38 also changes. These are arranged in such a way that at a certain angle, at which the upper body element 4 is twisted relative to the pelvic element 6, the polarity of the magnets 38 changes, so that an attractive force acts between the magnets 34 and 38 up until this angle and a repelling force acts from this angle and beyond. At the point at which an attractive force becomes a repelling force, the first force transmission element 26 moves out of the position shown in FIG. 3 and engages with the second force transmission element 28.

A locking device 44, which can be displaced in the circumferential direction, can be used to fix the position of the first force transmission device 26 relative to the second force transmission device, so that a displacement of one of the two force transmission elements is no longer possible. This prevents the two force transmission elements 26, 28 from either engaging or disengaging.

Figure 5:
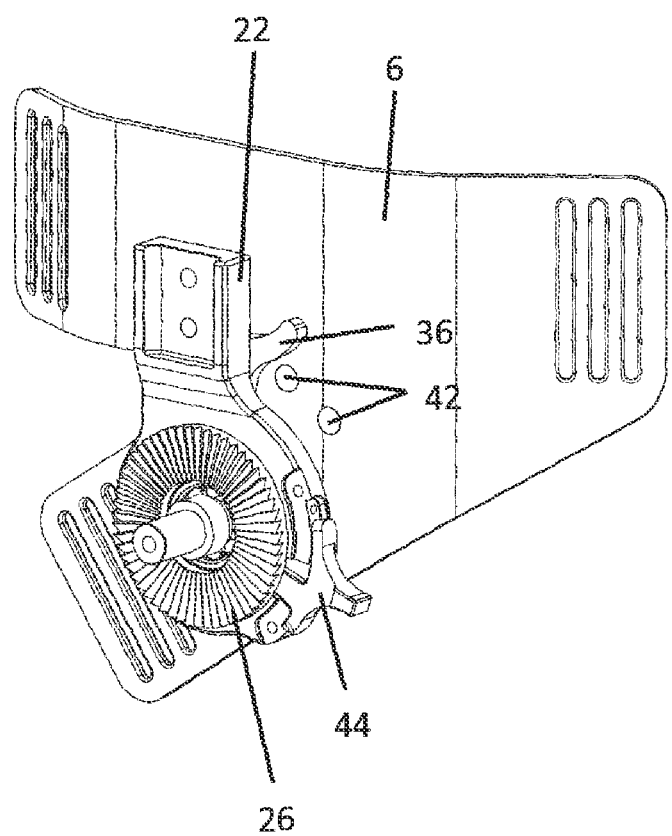

FIG. 5 depicts a section of the elements shown in FIG. 4 in a partially mounted representation. The displacement device 36 is found on the pelvic element 6. Two countermagnets 42 and the first force transmission element 26 are also visible. The first force transmission element 26 can be fixed relative to the second connection element 22 via the locking device 44.

Figure 6:
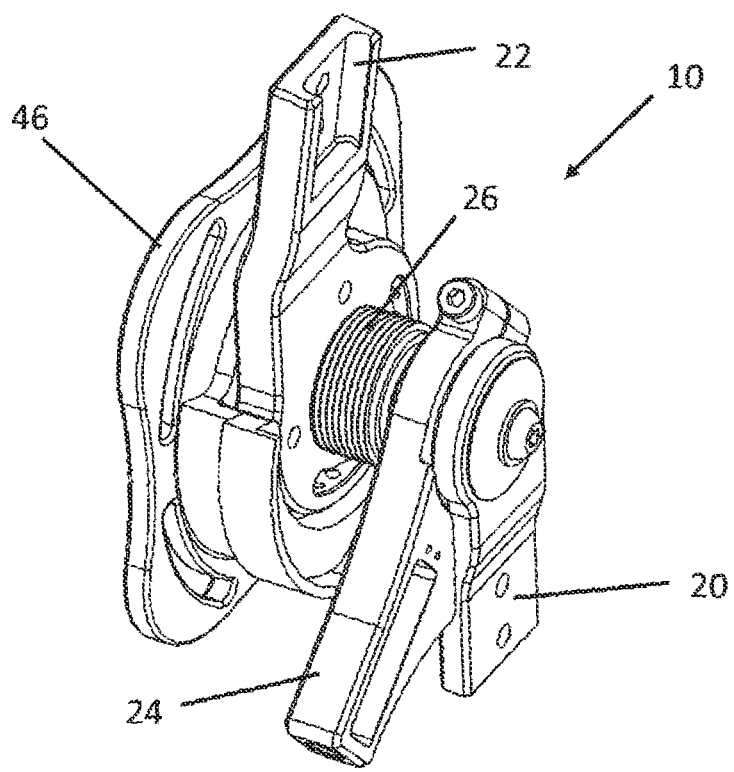

FIG. 6 depicts a joint device 10 for an orthopaedic device according to a further example of an embodiment of the present invention. It also features a second connection element 22, a first connection element 20 as well as a lever 24, and is positioned on a pelvic element 6, not depicted, via a mounting plate. In the example of an embodiment shown, the first force transmission element 26 is designed as a wrap spring 36. The second force transmission element 28 is not shown in FIGS. 6 and 7, and is designed as a rod or shaft that extends inside the wrap spring 26.

Figure 7:
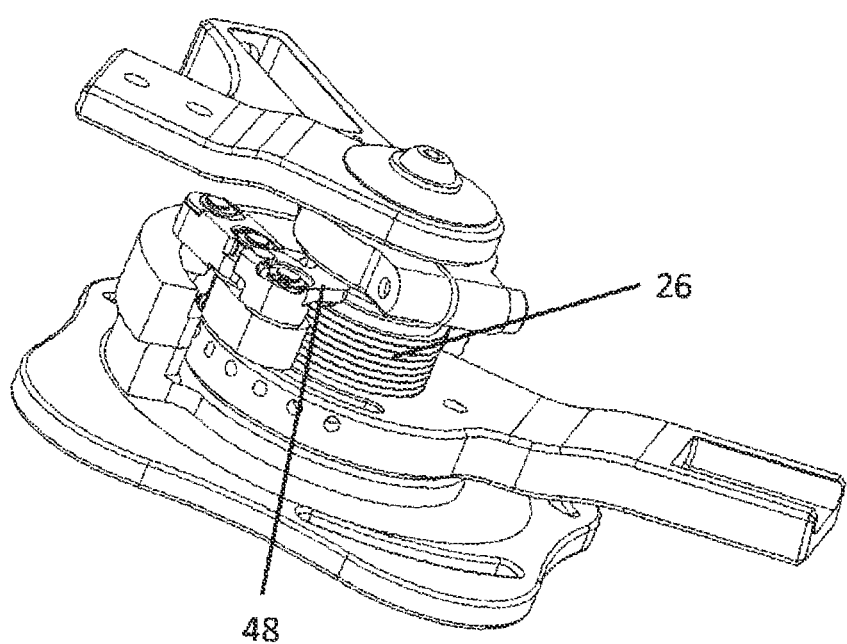
Figure 8:
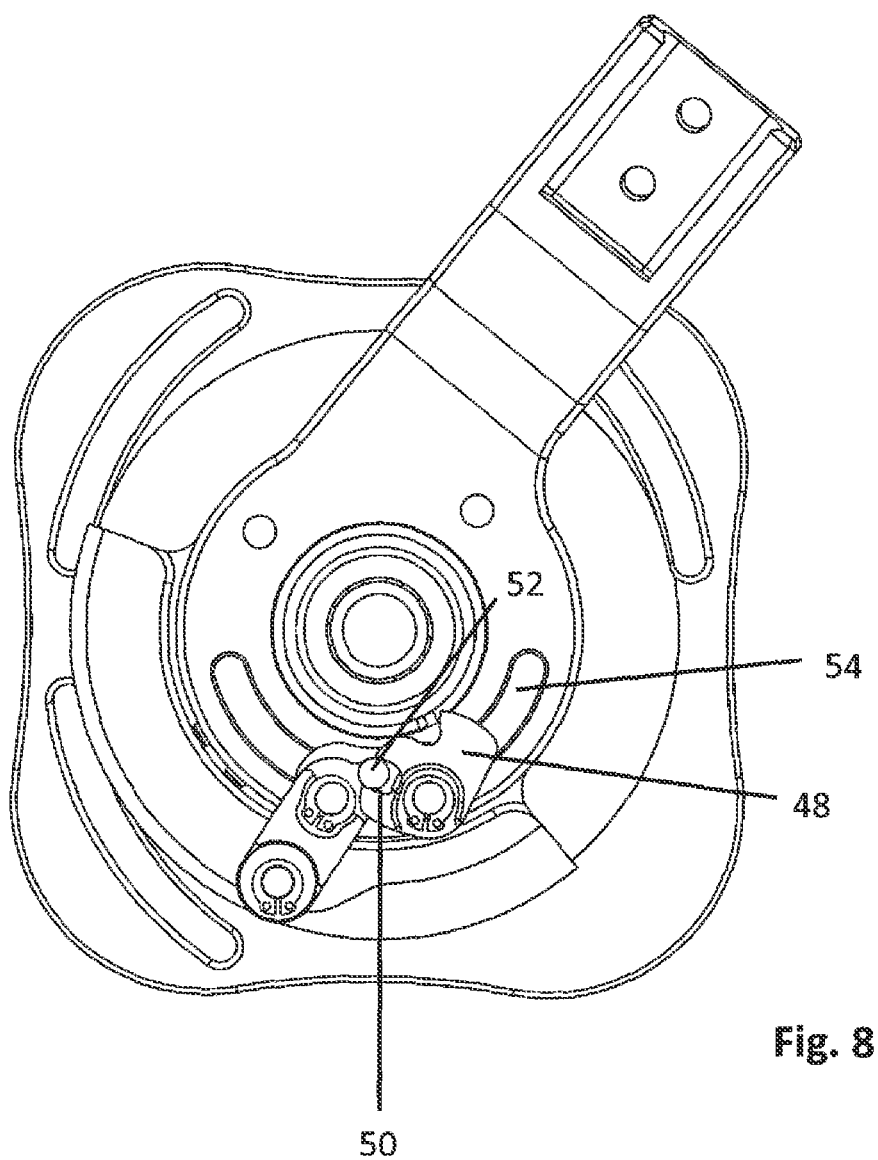

FIG. 7 depicts the device from FIG. 6 from another angle. One recognizes the first force transmission element 26. A driver 48 is situated on the upper leg element 2; said driver can be more clearly seen in the partially dismantled representation in FIG. 8. It features a recess 15, in which a pin 52 engages when the pin 52 is moved relative to the recess 50 of the driver 48. This occurs along a curved elongated hole 54. Once the pin 52 has engaged with the recess 50, a further movement of the two components causes the wrap spring to be moved such that its cross-section reduces. This leads to a friction connection between the first force transmission element, designed as a wrap spring, and the second force transmission element 28, designed as a shaft and situated inside the wrap spring 26.

Figure 9:
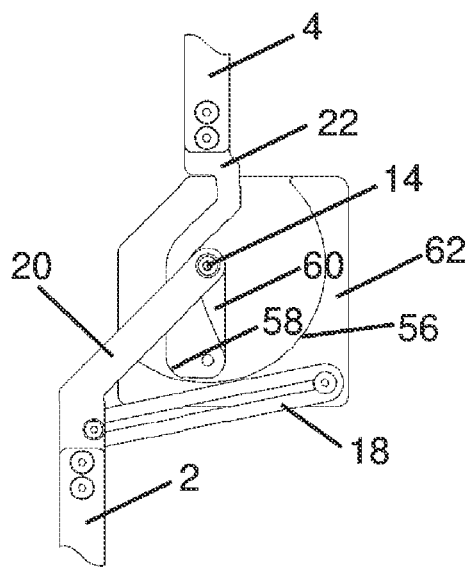

FIG. 9 shows a schematic representation of a further joint device. A section of the upper leg element 2 is depicted on the first connection element 20. A section of the upper body element 4 is found on the second connection element 22. A housing 62 is depicted between them. The mechanical energy store 18 is arranged between the first connection element 20 and the housing 62 in the form of an elastic element, wherein said housing is arranged on a pelvic element 6, not depicted, such that it is pivotable.

In the example of an embodiment shown, a circular friction profile is found on the housing 62. The first connection element 20 and thus the upper leg element 2 arranged on it are arranged on the pelvic element 6, not depicted, such that it can be swivelled about the first swivel axis 14. The second connection element 22 features a friction projection 58 and is arranged via a lever 60 on the pelvic element 6 such that it can be swivelled about the same swivel axis 14. In the example of an embodiment shown, the friction projection 58 forms the first force transmission element and the friction profile 56 the second force transmission element 28.

FIG. 9 depicts the situation in which there is a gap between the friction projection 58 and the friction profile 56, so that a frictional connection between the two does not occur. In this state, if an upper leg, which is connected to the upper leg element 2, is raised, it is twisted clockwise about the first swivel axis 14 in the representation depicted. The housing 62 is also swivelled about the swivel axis 14 by way of the mechanical energy store 18. As there is no frictional connection between the two force transmission elements 26, 28, the mechanical energy store 18 is not charged.

Figure 10:
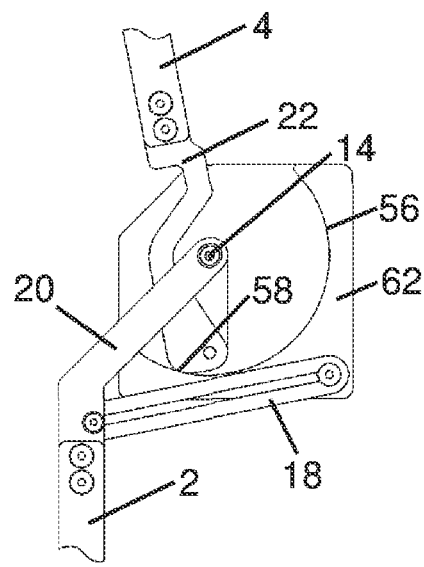

FIG. 10 depicts the situation in which the upper body element 4 has been swivelled relative to the pelvic element 6, which is also not depicted in FIG. 10, because, for instance, the wearer of the orthopedic device has bent forward. The upper body element 4 has therefore been swivelled anti-clockwise relative to the pelvic element 6. This causes the friction projection 58 of the second connection element 22 to come into contact with the friction profile 56 of the housing 62; It is pushed against said friction profile such that a frictional connection occurs between the two elements. If, in this situation, the upper leg is raised, i.e. the upper leg element 2 is swivelled clockwise about the swivel axis 14, the housing 62 can no longer be swivelled relative to the upper body element 4 due to the frictional connection. Instead, the mechanical energy store 18 is charged and the elastic element stretched. This generates a force which supports the wearer when straightening up, i.e. the anti-clockwise swivelling of the upper leg element 2.

Figure 11:
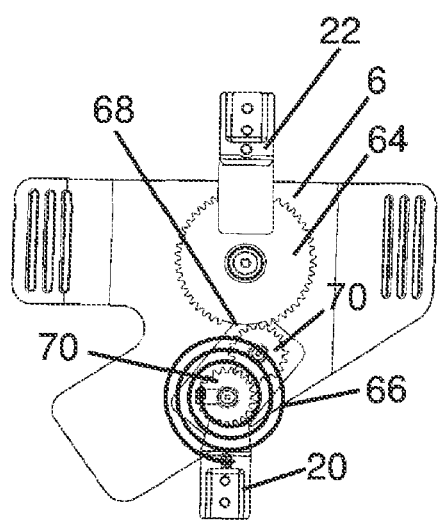
Figure 12:
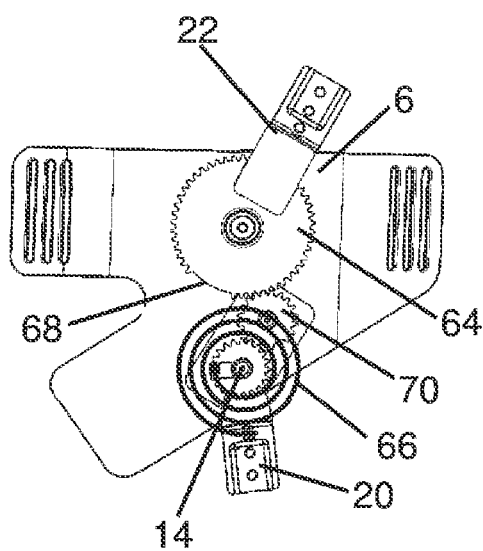

FIGS. 11 and 12 show a further example of an embodiment. The second connection element 22 is arranged on the pelvic element 6 via a rotatable gearwheel 64. A spiral spring 66 is arranged on the first connection element 20, on which the upper leg element 2, not depicted in FIGS. 11 and 12, can be arranged. It is clear that the gearwheel has a toothless area. FIG. 11 shows the situation in which the upper leg element 12 and the first connection element 20 can be swivelled anti-clockwise without charging the spiral spring 66. In this case, the small gearwheels 70 are rotated. Given that the upper of the small gearwheels 70 lies, with its teeth, in the toothless area 68 of the gearwheel 64, this small gearwheel 70 is not engaged with the gearwheel 64, so that the small gearwheels 70 can be rotated without charging the spiral spring 66.

FIG. 12 depicts a different situation in which the upper body element 4, which is to be arranged on the second connection element 22, has been swivelled relative to the hip element 6. This also causes the gearwheel 64 to rotate about its rotational axis, so that a toothed area, rather than the toothless area 68, engages with the upper small gearwheel 70. If, in this situation, the upper leg element 2 with the first connection element 20 is swivelled and swivelled anti-clockwise about the first swivel axis 14, the spiral spring 66 is charged.

Figure 13:
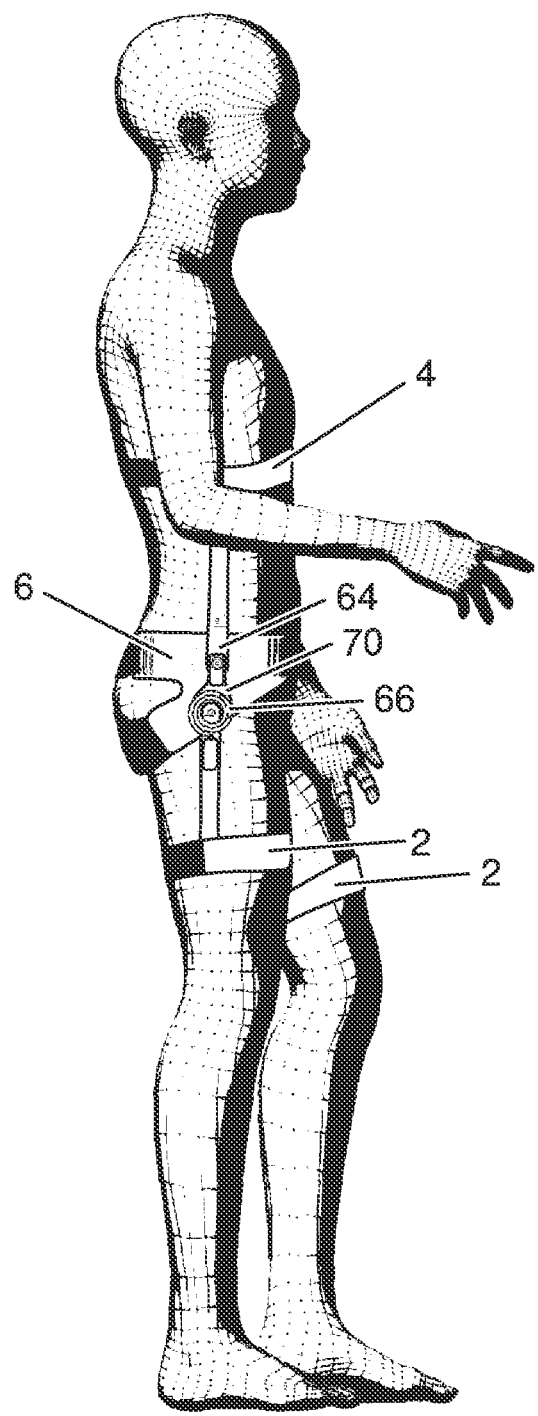
Figure 14:
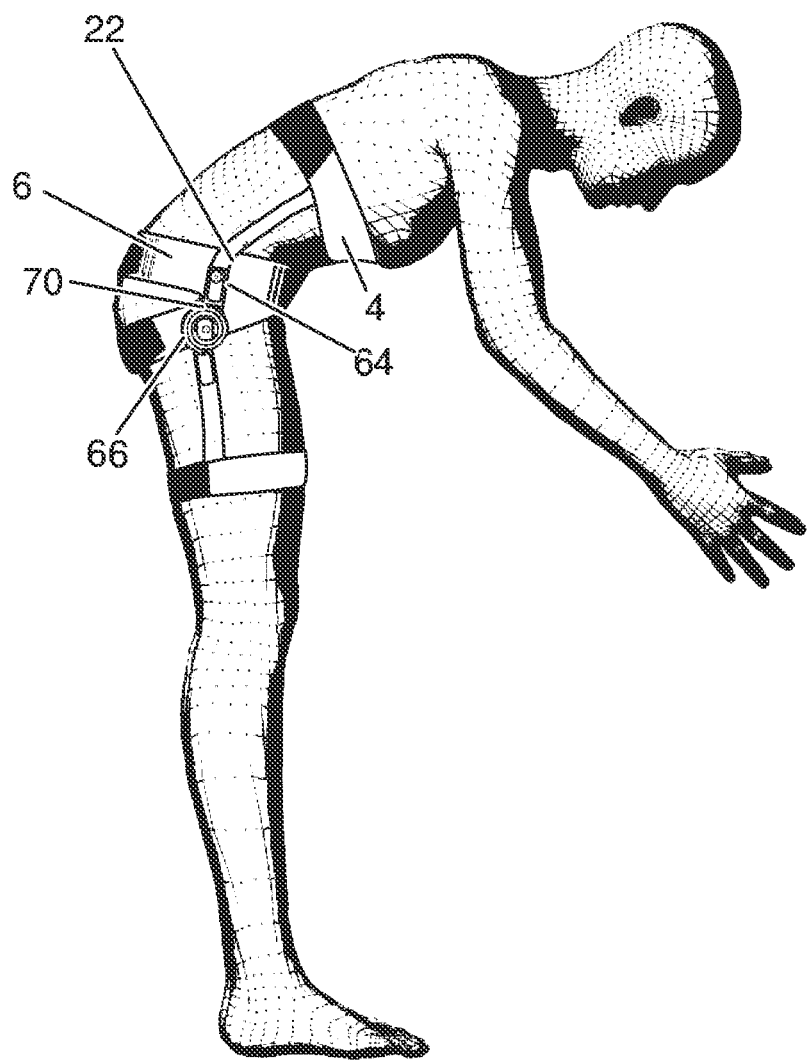
Figure 15:
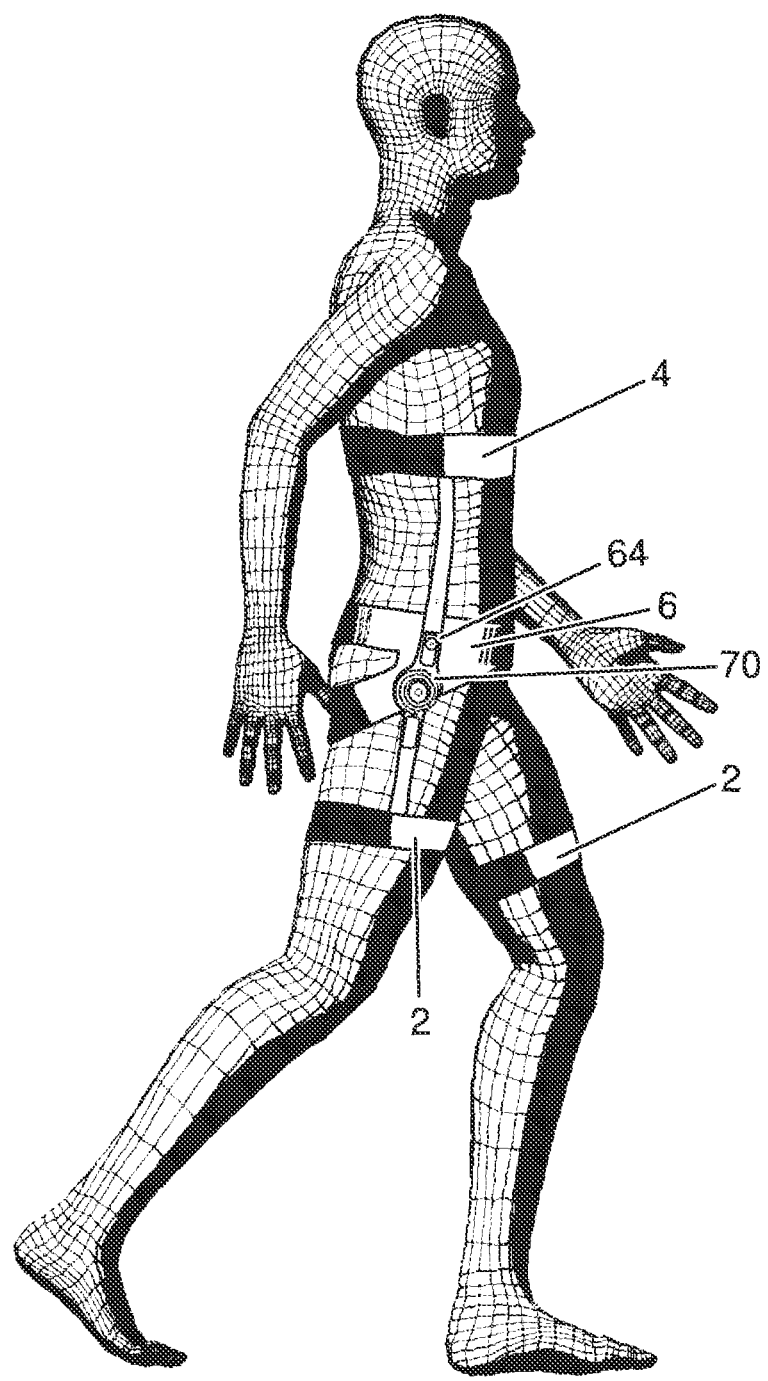

FIGS. 13 to 15 depict the device with the elements from FIGS. 11 and 12 in different positions in the applied state. In each case, one recognizes an upper leg element 2, an upper body element 4 as well as the hip element 6, on which the spiral spring 66 and the gearwheel 64 in particular can be recognized. FIG. 13 depicts the wearer of the device in an upright position. Due to its toothless area 68, the gearwheel 64 is not engaged with the small gearwheel 70, such that the spiral spring 66 is not tensioned, regardless of the position of the upper leg element 2.

FIG. 14 depicts the situation in which the wearer of the device has bent his torso forwards. As a result, the upper body element 4 with the second connection element 22 is swivelled relative to the pelvic element 6. The gearwheel 64 is rotated about its swivel axis and now engages with the teeth of the small gearwheel 70, so that the spiral spring 66 is tensioned as of this point. Of course, the upper leg does not necessarily need to be moved to tension the spiral spring 66. It is also possible to further lower the upper body in order to tension the energy store 18, i.e. the spiral spring 66 in the example of an embodiment shown.

FIG. 15 shows the person walking. In this case, the upper body and the upper body element 4 are also not swivelled relative to the hip joint, so that the gearwheel 64 is not engaged with the upper small gearwheel 70 and the spiral spring 66 is therefore not tensioned.

We claim:

1. An orthopedic device for supporting a lower back of a user, wherein the device comprises:
    an energy store,
    a pelvic element,
    an upper body element with a first force transmission element, and
    an upper leg element with a second force transmission element,
wherein
    the upper leg element is arranged on the pelvic element such that the upper leg element is swivelled about a first swivel axis,
    the upper body element is movably arranged relative to the pelvic,
    the first force transmission element is engaged and disengaged with the second force transmission element by moving the upper body element relative to the pelvic element, and the energy store is discharged by swivelling the upper leg element relative to the upper body element when the first force transmission element is engaged with the second force transmission element, wherein, in an active state, the first force transmission element and the second force transmission element are automatically engaged or disengaged by moving the upper body element relative to the pelvic element, and wherein, in a passive state, the first force transmission element and the second force transmission element are not automatically engaged or disengaged by moving the upper body element relative to the pelvic element.

2. The orthopedic device according to claim 1, wherein the first force transmission element comprises a gearwheel that is eccentrically arranged on the pelvic element such that the gearwheel is swivelled about a second swivel axis.

3. The orthopedic device according to claim 2, wherein the upper body element is connected to the first force transmission element such that the first force transmission element is swivelled about the second swivel axis when the upper body element is moved relative to the pelvic element.

4. The orthopedic device according to claim 2, wherein the upper body element and the first force transmission element feature connection elements that correspond with one another, so that the upper body element is connected to the first force transmission element in a plurality of positions.

5. The orthopedic device according to claim 1, wherein the device has a displacement device that is configured to move the first force transmission element and/or the second force transmission element towards one another when the upper body element assumes an angle in relation to the pelvic element that is smaller than a pre-determined threshold angle.

6. The orthopedic device according to claim 5, wherein the displacement device is configured to move the first force transmission element and/or the second force transmission element away from one another when the upper body element assumes an angle in relation to the pelvic element that is greater than the pre-determined threshold angle.

7. The orthopedic device according to claim 5, wherein at least two magnets are arranged on one of the pelvic element or the upper leg element and at least one magnet is arranged on the respective other one of the pelvic element or the upper leg element in such a way that at least one of the at least two magnets exert a force on the other of the at least two magnets, a direction of the force changes when, during a movement of the upper body element relative to the pelvic element, the angle passes the pre-determined threshold angle.

8. The orthopedic device according to claim 1, wherein the device features at least one activation element, an activation of the at least one activation element allows for the device to be brought from the active state into the passive state, and/or from the passive state into the active state.

9. The orthopedic device according to claim 1, wherein the energy store comprises at least one spiral spring.

10. An orthopedic device for supporting a lower back of a user, the device comprising:
    a energy store;
    a pelvic element;
    an upper body element with a first force transmission element; and
    an upper leg element with a second force transmission element;
    wherein:
    the upper leg element is arranged on the pelvic element such that the upper leg element is configured to be swiveled about a first swivel axis,
    the upper body element is movably arranged relative to the pelvic element,
    the first force transmission element is configured to be engaged and disengaged with the second force transmission element by moving the upper body element relative to the pelvic element, the first force transmission element comprising a gearwheel that is eccentrically arranged on the pelvic element such that the first force transmission element is configured to be swiveled about a second swivel axis, and
    the energy store is configured to be discharged by swiveling the upper leg element relative to the upper body element when the first force transmission element is engaged with the second force transmission element, wherein the device is configured to be brought into an active state, in which the first force transmission element is configured to be engaged and disengaged with the second force transmission element by moving the upper body element relative to the pelvic element, and into a passive state.

11. The orthopedic device according to claim 10, wherein the upper body element is connected to the first force transmission element such that the first force transmission element is swiveled about the second swivel axis when the upper body element is moved relative to the pelvic element.

12. The orthopedic device according to claim 10, wherein the upper body element and the first force transmission element feature connection elements that correspond with one another, so that the upper body element is configured to be connected to the first force transmission element in a plurality of positions.

13. The orthopedic device according to claim 10, further comprising a displacement device that is configured to move at least one of the first force transmission element and the second force transmission element towards one another when the upper body element assumes an angle in relation to the pelvic element that is smaller than a pre-determined threshold angle.

14. The orthopedic device according to claim 13, wherein the displacement device is configured to move at least one of the first force transmission element and the second force transmission element away from one another when the upper body element assumes an angle in relation to the pelvic element that is greater than the pre-determined threshold angle.

15. The orthopedic device according to claim 13, wherein at least two magnets are arranged on one of the pelvic element or the upper leg element and at least one magnet is arranged on the respective other one of the pelvic element or the upper leg element in such a way that one of the at least two magnets exert a force on the other of the at least two magnets, the direction of the force changes when, during a movement of the upper body element relative to the pelvic element, the angle passes the pre-determined threshold angle.

16. The orthopedic device according to claim 10, wherein the device is configured to be brought into an active state, in which the first force transmission element is configured to be engaged and disengaged with the second force transmission element by moving the upper body element relative to the pelvic element, and into a passive state.

17. The orthopedic device according to claim 10, wherein the energy store has at least one battery.

18. The orthopedic device according to claim 10, wherein the energy store has at least one spiral spring.

19. An orthopedic device to support a lower back of a user, the device comprising:
a energy store;
a pelvic element configured to contact a pelvis of the user;
an upper body element with a first force transmission element, the upper body element configured to be mounted to an upper body of the user, wherein the first force transmission element comprises a gearwheel that is eccentrically arranged on the pelvic element such that the gearwheel is moved about a second swivel axis;
an upper leg element with a second force transmission element, the upper leg element configured to be mounted to an upper leg of the user;
wherein the upper leg element is arranged on the pelvic element such that the upper leg element is movable about a first axis, the upper body element is adjustable relative to the pelvic element to engage and disengage the first force transmission element with the second force transmission element, and the energy store is discharged by moving the upper leg element relative to the upper body element when the first force transmission element is engaged with the second force transmission element, wherein the device is configured to be brought into an active state, in which the first force transmission element is configured to be engaged and disengaged with the second force transmission element by moving the upper body element relative to the pelvic element, and into a passive state.

* * * * *